United States Patent [19]

Forhetz et al.

[11] Patent Number: 5,046,604
[45] Date of Patent: Sep. 10, 1991

[54] ODOR-ABSORBING LINER

[76] Inventors: Dawn V. Forhetz; Scott A. Forhetz, both of 609 E. Main St., Collinsville, Ill. 62234

[21] Appl. No.: 632,929

[22] Filed: Dec. 24, 1990

[51] Int. Cl.⁵ .................... A41B 9/04; F17S 13/00; B65D 75/28
[52] U.S. Cl. .................... 206/0.5; 424/76.1; 206/484.1; 206/524.5; 206/205
[58] Field of Search .................. 206/204, 205, 524.5, 206/0.5, 484.1; 220/908, 909; 424/76.1, 76.4, 76.5

[56] References Cited

U.S. PATENT DOCUMENTS

| 885,778 | 4/1908 | Neuberger | 206/0.5 X |
|---|---|---|---|
| 4,124,116 | 11/1978 | McCabe, Jr. | 206/204 |
| 4,244,059 | 1/1981 | Pflaumer | 424/76.1 X |
| 4,676,196 | 6/1987 | Lojek | 119/1 |
| 4,706,845 | 11/1987 | Schnurer | 221/102 |
| 4,756,939 | 7/1988 | Goodwin | 206/204 X |
| 4,790,051 | 12/1988 | Knight | 27/28 |
| 4,840,770 | 6/1989 | Walz | 422/40 |
| 4,864,740 | 9/1989 | Oakley | 36/44 |

FOREIGN PATENT DOCUMENTS

| 2221353 | 9/1987 | Japan | 424/76.1 |
|---|---|---|---|
| 1516845 | 7/1978 | United Kingdom | 206/205 |

Primary Examiner—William I. Price
Attorney, Agent, or Firm—Don W. Weber

[57] ABSTRACT

An odor-absorbing shelf liner is presented which is made up of upper and lower sheets stitched together to form discreet pouches. Inside each pouch is an odor-absorbing material such as baking soda. When the liner is placed on the shelf of a refrigerator, cabinet or drawer it not only serves as a shelf liner but also serves as an odor-absorbing device.

3 Claims, 1 Drawing Sheet

ODOR-ABSORBING LINER

BACKGROUND OF THE INVENTION

This invention relates to the field of odor-absorbing materials used in drawers, refrigerators, or other household containers. More particularly it relates to a drawer or shelf liner containing odor-absorbing material.

Various odors from vegetables, meats, and other foods often permeate the kitchen area. These odors build up particularly in drawers or in refrigerators where the odor is contained by the sides and doors. Previous devices used to contain this odor include a common box of baking soda or other deodorizers or scent-giving devices which would either absorb the odor or mask the odor by producing another scent.

This device is designed not only to absorb the odor in a shelf or drawer of a cabinet, but may also be conveniently used to line the shelf or cabinet and thus to provide an appealing base upon which to place items.

BRIEF DESCRIPTION OF THE INVENTION

This invention comprises essentially two porous sheets which are stitched together to form a quilted pattern. The stitching is not only along the outer edges of the two sheets but also in the central area. This creates a number of pouches. Into the pouches is placed a discreet amount of baking soda or other odor-absorbing material. The sheet thus produced may be used to line shelves, drawers or the shelves of refrigerators. It serves not only as a shelf liner but also as an odor-absorber.

DETAILED DESCRIPTION OF THE PREFERRED EMBODIMENT

The embodiment of this invention is simple yet unique. This invention will provide an effective means of containing odor in the kitchen or other areas while at the same time providing a convenient liner upon which to place items.

Figure 1:
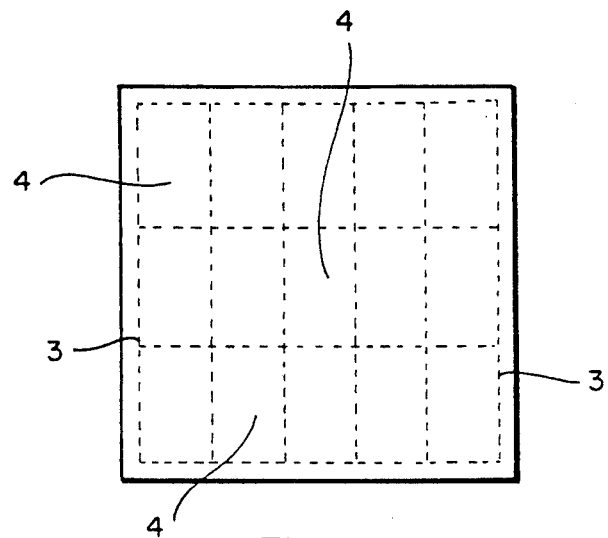
FIG. 1 is a top plan view of the shelf liner.
Figure 2:
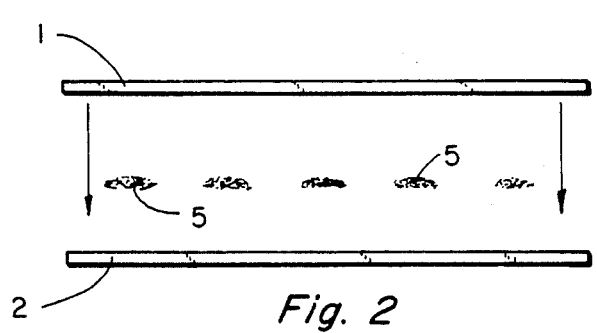
FIG. 2 is an enlarged exploded view of the device showing the upper and lower layers and the individual amounts of odor-absorbing material.
Figure 3:
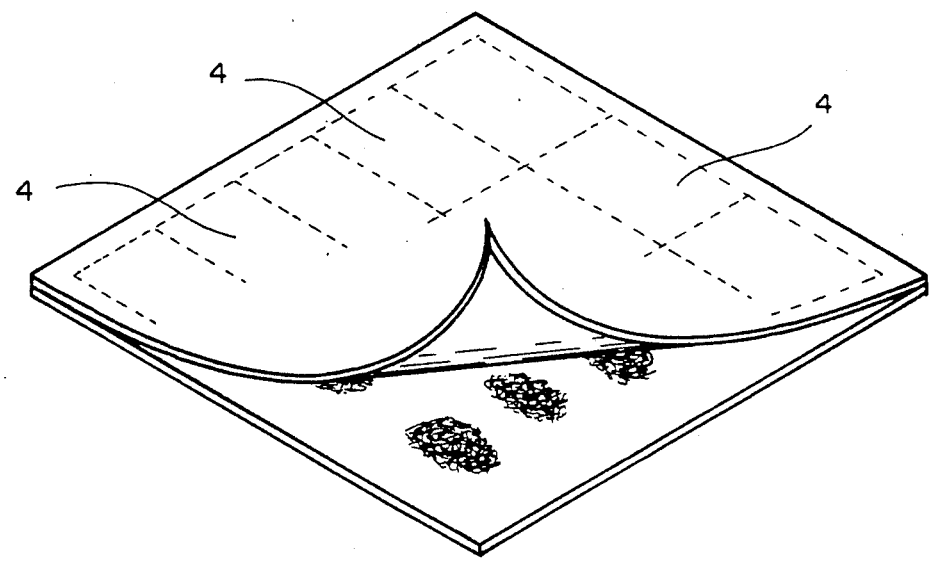
FIG. 3 is an enlarged perspective view of the device with the top layer partially removed showing the baking soda which is placed into the pouches.

The device has an upper 1 and lower 2 layer of porous material. This material may be made of paper, cloth, or any other suitable material. The only characteristics of the upper and lower layers which are critical is that it be capable of being fastened together and that it allow odors to drift in from the outside environment into the inner pouches The upper and lower layers of the device are stitched together as best shown in FIGS. 1 and 3.

The stitching 3 (shown in the dotted lines on FIGS. 1 and 3) may be done in any convenient or decorative fashion. While horizontal and vertical stitching is shown, a quilt pattern of stitching or any other desirable pattern of stitching may be used. The object of the stitching however is not simply decorative. The stitching creates various pouches 4.

Before the two layers are completely stitched or sealed together, the pouches are filled with a discreet amount of baking soda 5 or other odor-absorbing material. The absorbing liner may have a number of pouches. In the preferred embodiment, each pouch contains a discreet amount of baking soda or other odor-absorbing material. In practice it has been found that sheets which are approximately twelve inches (12") square are preferred. These sheets are divided into sixteen separate pouches which are approximately three inches (3") square each. It has been found that approximately one-fourth (¼) cup of baking soda per twelve inch (12") square liner (or 16 pouches) produces the desirable results.

The seams and stitching 3 are preferred but the device itself may also be produced by creating pouches which are glued together or which are otherwise sealed. The purpose of creating a number of pouches is to prohibit the odor absorbing material from all collecting in one spot.

The particular type of material used for the upper and lower sheets is not critical. A paper towel will suffice, as will a light weight sheet of cloth. Any particular porous sheet which allows odor to go in and be absorbed by the odor-absorbing material is may be used.

It is to be noted that the dimensions provided herein are for purposes of illustration only and not for purposes of limitation. This particular shelf-liner could be produced in rolls or individual sheets of varying sizes. Additionally, more or less baking soda could be added to each pouch than that described in the preferred embodiment while still keeping within the contemplation of this invention. An odor-absorbing material other than baking soda may also be used.

Having fully described my invention, I claim:

1. An odor-absorbing drawer liner, comprising:
   (a) upper and lower porous sheets stitched together to form pouches;
   (b) an odor-absorbing material contained in at least one of said pouches.

2. An odor-absorbing drawer liner as in claim 1, wherein said odor-absorbing material is baking soda.

3. An odor-absorbing drawer liner as in claim 1, wherein each of said pouches contains a discreet amount of odor-absorbing material.

* * * * *